United States Patent
Ramesh

(10) Patent No.: US 11,917,305 B2
(45) Date of Patent: Feb. 27, 2024

(54) BLOOD FLOW IMAGING

(71) Applicant: Micron Technology, Inc., Boise, ID (US)

(72) Inventor: Vijay S. Ramesh, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 366 days.

(21) Appl. No.: 17/409,509

(22) Filed: Aug. 23, 2021

(65) Prior Publication Data

US 2023/0054862 A1  Feb. 23, 2023

(51) Int. Cl.
| | |
|---|---|
| *H04N 23/80* | (2023.01) |
| *G16H 30/20* | (2018.01) |
| *G06T 7/00* | (2017.01) |
| *G06F 3/06* | (2006.01) |
| *G16H 40/67* | (2018.01) |
| *G16H 20/60* | (2018.01) |
| *G16H 50/20* | (2018.01) |

(Continued)

(52) U.S. Cl.
CPC ........... *H04N 23/80* (2023.01); *G06F 3/0604* (2013.01); *G06F 3/0659* (2013.01); *G06F 3/0679* (2013.01); *G06T 7/0012* (2013.01); *G16H 20/60* (2018.01); *G16H 30/20* (2018.01); *G16H 30/40* (2018.01); *G16H 40/20* (2018.01); *G16H 40/67* (2018.01); *G16H 50/20* (2018.01); *G06T 2207/30104* (2013.01)

(58) Field of Classification Search
CPC ........ H04N 23/80; G16H 40/67; G16H 40/20; G16H 30/20; G16H 50/20; G16H 30/40; G16H 20/60; G06F 3/0604; G06F 3/0659; G06F 3/0679; G06T 7/0012; G06T 2207/30104
USPC .......................................................... 348/77
See application file for complete search history.

(56) References Cited

U.S. PATENT DOCUMENTS

| | | | |
|---|---|---|---|
| 9,329,129 B2 | 5/2016 | Pollak et al. | |
| 10,935,561 B2* | 3/2021 | Nguyen | G01N 27/3276 |

(Continued)

FOREIGN PATENT DOCUMENTS

WO   2009057014 A2   5/2009

*Primary Examiner* — Frantz B Jean
(74) *Attorney, Agent, or Firm* — Brooks, Cameron & Huebsch, PLLC

(57) ABSTRACT

A method for blood flow imaging can include receiving, by a processor coupled to a first memory device comprising a first type of media and a second memory device comprising a second type of media, an indication corresponding to initiation of an application and data captured by an imaging device coupled to the processor. The method can include determining characteristics of a workload corresponding to execution of the application to process the data captured by the imaging device for the first memory device and the second memory device and writing the data captured by the imaging device to the first memory device or the second memory device based on determined characteristics for the first memory device and the second memory device in executing the workload. The method can further include executing the workload as part of executing of the application while the data captured by the imaging device is written to the first memory device or the second memory device that exhibits greater than the threshold set of determined characteristics in executing the workload.

25 Claims, 5 Drawing Sheets

(51) Int. Cl.
  *G16H 30/40* (2018.01)
  *G16H 40/20* (2018.01)

(56) References Cited

U.S. PATENT DOCUMENTS

2022/0392065 A1* 12/2022 Min ....................... A61B 6/032
2023/0113721 A1* 4/2023 Kassel .................. G06T 7/0016
                                                              382/128

* cited by examiner

US 11,917,305 B2

BLOOD FLOW IMAGING

TECHNICAL FIELD

The present disclosure relates generally to semiconductor memory and methods, and more particularly, to apparatuses, systems, and methods for blood flow imaging.

BACKGROUND

Memory devices are typically provided as internal, semiconductor, integrated circuits in computers or other electronic systems. There are many different types of memory including volatile and non-volatile memory. Volatile memory can require power to maintain its data (e.g., host data, error data, etc.) and includes random access memory (RAM), dynamic random access memory (DRAM), static random access memory (SRAM), synchronous dynamic random access memory (SDRAM), and thyristor random access memory (TRAM), among others. Non-volatile memory can provide persistent data by retaining stored data when not powered and can include NAND flash memory, NOR flash memory, and resistance variable memory such as phase change random access memory (PCRAM), resistive random access memory (RRAM), and magnetoresistive random access memory (MRAM), such as spin torque transfer random access memory (STT RAM), among others.

Memory devices may be coupled to a host (e.g., a host computing device) to store data, commands, and/or instructions for use by the host while the computer or electronic system is operating. For example, data, commands, and/or instructions can be transferred between the host and the memory device(s) during operation of a computing or other electronic system.

DETAILED DESCRIPTION

Figure 1:
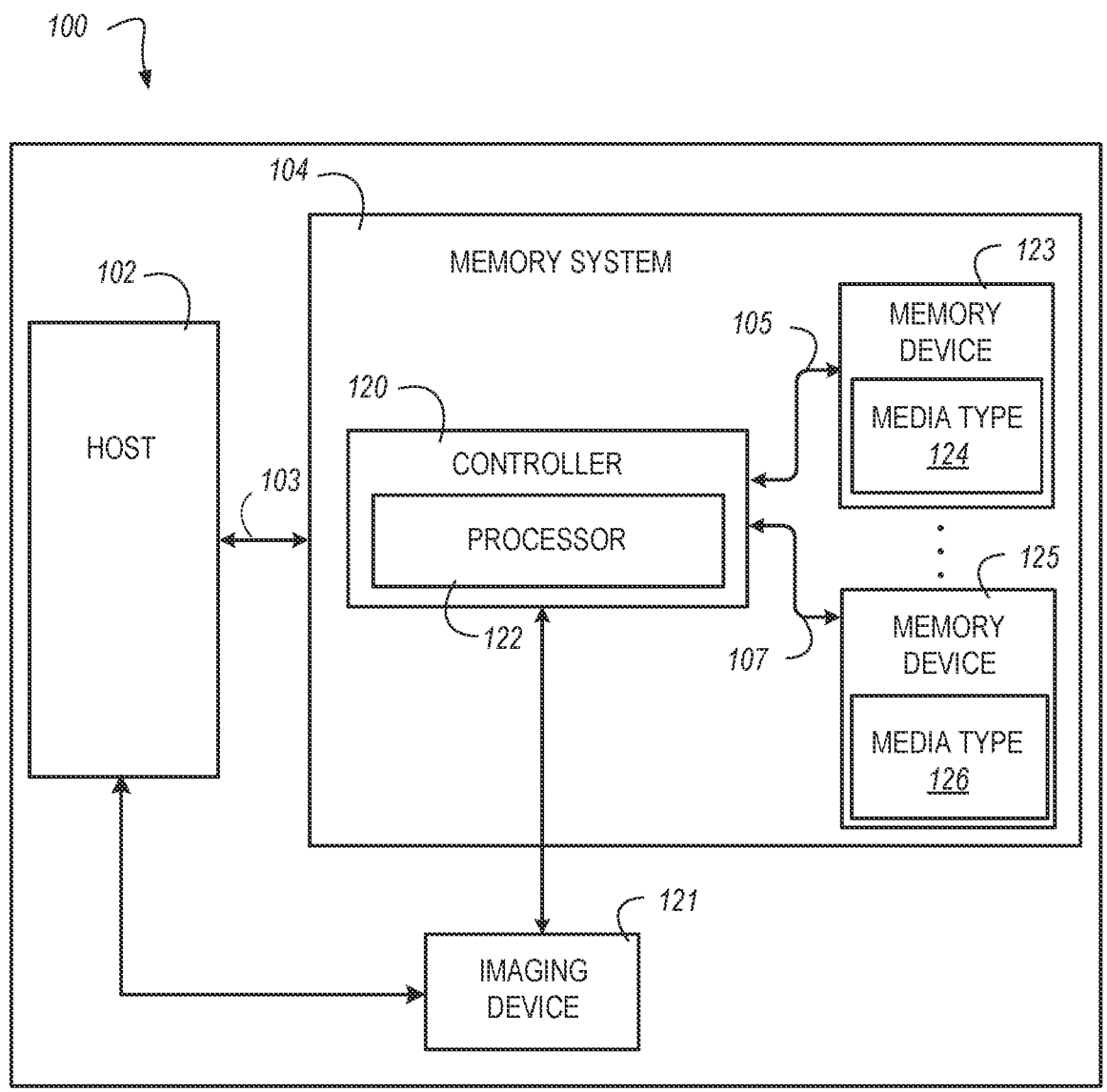
FIG. 1 is a functional block diagram in the form of an apparatus including a host and a memory device in accordance with a number of embodiments of the present disclosure.

Methods, systems, and apparatuses related to blood flow imaging are described. For example, a method for blood flow imaging can include receiving, by a processor coupled to a first memory device comprising a first type of media and a second memory device comprising a second type of media, an indication corresponding to initiation of an application and data captured by an imaging device coupled to the processor. The method can include determining characteristics of a workload corresponding to execution of the application to process the data captured by the imaging device for the first memory device and the second memory device and writing the data captured by the imaging device to the first memory device or the second memory device based on determined characteristics for the first memory device and the second memory device in executing the workload. The method can further include executing the workload as part of executing of the application while the data captured by the imaging device is written to the first memory device or the second memory device that exhibits greater than the threshold set of determined characteristics in executing the workload.

Blood imaging techniques can be performed to detect abnormalities in the blood of a living creature (e.g., a human or other animal that has blood veins through which blood vessels flow). In general, these techniques can involve the use of magnetic resonance imaging (MRI) techniques such as magnetic resonance angiography (MRA) and/or computed tomography (CT) techniques such as computed tomography angiography (CTA), among other suitable techniques. Although these techniques are generally reliable at detecting abnormalities in the blood, they are costly and time-consuming procedures to undergo. In addition, such procedures require that the living creature be inserted into a very large, specialized device, typically in a hospital or office of a doctor that specializes in the operation of such devices, and therefore require that the living creature be present at the hospital or at the office of the doctor that specializes in the operation of the aforementioned devices.

However, as imaging device and computing (e.g., processing and memory device) technology evolves, it is possible to perform blood imaging techniques in the absence of the large, specialized devices described above that are traditionally required to perform blood imaging techniques, such as MRA and/or CTA. For example, as described in more detail herein, embodiments of the present disclosure can allow for blood imaging to be performed techniques to detect abnormalities in the blood of a living creature using a mobile computing device. Such abnormalities can include blood cells that exhibit characteristics indicative of blood cancers (e.g., leukemia, lymphoma myeloma, etc.), fluctuating blood glucose levels, fluctuating blood pressure levels, percentages of white blood cells versus red blood cells, hemophilia, and/or anemia, among other abnormalities. As used herein, the term "mobile computing device" generally refers to a handheld computing device (e.g., a smartphone) that has a slate or phablet form factor. In general, a slate form factor can include a display screen that is between approximately 3 inches and 5.2 inches (measured diagonally), while a phablet form factor can include a display screen that is between approximately 5.2 inches and 7 inches (measured diagonally). Examples of "mobile computing devices" are not so limited, however, and in some embodiments, a "mobile computing device" can refer to an IoT device, among other types of edge computing devices.

In order to perform blood imaging techniques in the absence of the large, specialized devices described above, aspects of the present disclosure provide for dynamic allocation of computing resource (e.g., processing and/or memory resources) to free up computing resources that exhibit particular characteristics to allow for capture and processing of images to perform blood imaging techniques. As described in more detail, herein, the computing resources can be reallocated (or pre-allocated) in response to a determination (e.g., based on receipt of an application initiation indicator) that an application that involves the capture and processing of images to perform blood imaging techniques is to be executed. This reallocation (or pre-allocation) of computing resources can seek to optimize available computing resources to capture, store, and/or process images to perform blood imaging techniques to make the processing of such images possible.

For example, due to the high level of quality such images need to have in order to be processed in connection with blood imaging techniques, the images can have exceptionally large file sizes and can therefore be best processed using computing resources that exhibit high bandwidth characteristics, low access latency characteristics, high memory cell density characteristics, and/or low error characteristics, among others. By reallocating (or pre-allocating) computing resources based on such characteristics in response to a determination that an application that involves the capture and processing of images to perform blood imaging techniques is to be executed, aspects of the present disclosure can facilitate performance of blood imaging techniques in the absence of the very large, specialized devices that are commonly used to perform blood imaging.

In addition, aspects of the present disclosure allow for information gleaned for performance of the blood imaging operations described herein to be stored (e.g., stored over time to create a long-term record of abnormalities, or the lack thereof, detected during performance of the blood imaging operations), transferred (e.g., to a hospital, doctor, emergency care provider, etc.), and/or analyzed to generate health recommendations (e.g., dietary recommendations, exercise and/or activity recommendations, vitamin/supplement recommendations, and the like).

As mentioned above, embodiments of the present disclosure allow for the execution of an application to perform blood imaging techniques. As used herein, the term "application" generally refers to one or more computer programs that can include computing instructions that are executable to cause a computing system to perform certain tasks, functions, and/or activities. An amount of computing resources (e.g., processing resources and/or memory resources) consumed in execution of an application can be measured in terms of a "workload." As used herein, the term "workload" generally refers to the aggregate computing resources consumed in execution of applications that perform a certain task, function, and/or activity. During the course of executing an application, multiple sub-applications, sub-routines, etc. may be executed by the computing system. The amount of computing resources consumed in executing the application (including the sub-applications, sub-routines, etc.) can be referred to as the workload.

Some applications that can give rise to demanding workloads include applications that process data, such as images and/or video, in real time. Such applications, especially when processing of high-quality images and/or video in real time to correct imperfections in images and/or video are requested, can request usage of a large quantity of computing resources, and therefore create a demanding workload. Some examples of these kinds of applications can include medical diagnostic imaging applications, which can include examination of particular parts of a living creature, such as a human body that are captured with images and/or video in real time and processed to perform blood imaging techniques.

As workloads become increasingly demanding, especially in light of improvements to broadband cellular network technology, issues associated with optimization of workload handling can become further exacerbated in mobile computing devices (e.g., smartphones, tablets, phablets, and/or Internet-of-Things (IoT) devices, among others) where physical space constraints can dictate the amount of processing resources and/or memory resources available to the device. In addition, execution of demanding workloads using mobile computing devices can, in some approaches, quickly drain battery resources available to the mobile computing device and/or cause unwanted thermal behavior (e.g., the mobile computing device can become too hot to operate in a stable manner, etc.) for the mobile computing device.

As broadband cellular network technology evolves, higher resource demands may be placed on devices connected to a broadband cellular network. This can be due to increases in available bandwidth associated with broadband cellular networks (referred to herein for brevity as "networks"), which can, in turn, give rise to higher download speeds and therefore increased data traffic associated with devices connected to the network. Such increased data traffic can further give rise a greater quantity of data be received, stored, and/or processed within devices connected to the network.

In addition, the potential for increased data traffic involving devices, such as mobile computing devices, connected to the network can allow for increasingly complicated applications (e.g., computing applications that are designed to cause a computing device to perform one or more specific functions or tasks) to be executed on the devices. Execution of such applications can in turn give rise to demanding workloads, which can strain computing resources and, more specifically, strain computing resources that are allocated in some conventional approaches.

In order to attempt to execute demanding workloads on mobile computing devices, some approaches can include throttling performance of the mobile computing device during execution of some kinds of workloads to ensure sufficient computing resources are available to execute demanding workloads. In addition, some approaches can include throttling performance of the mobile computing device during execution of some kinds of workloads in an attempt to mitigate adverse effects on battery consumption and/or thermal behavior. However, such approaches may therefore only use a subset of the available computing resources and/or may not be able to take advantage of the available computing resources. This can be especially problematic in mobile computing devices which, as mentioned above may already feature diminished computing resources due to space constraints in comparison with, for example, a desktop computing device.

In contrast, embodiments described herein can provide hardware circuitry (e.g., a controller, processor, etc.) that can monitor and/or determine characteristics of workloads executed in a computing system or mobile computing device when data corresponding to the workloads is stored in different types of memory devices. The hardware circuitry can, based on the monitored or determined characteristics of the workloads, write at least a portion of the workload to a different type of memory device. For example, if the workload is executed while the data corresponding to the workload is stored in a volatile memory device and the hardware circuitry determines that execution of the workload can be optimized if the data corresponding to the workload is stored in a non-volatile memory device, the hardware circuitry can cause at least a portion of the data corresponding to the workload to be written to the non-volatile memory device. Such dynamic determination of workload characteristics and subsequent allocation of workloads to memory devices that include different types of media can be especially beneficial in mobile computing systems, especially as increasingly processing resource intensive workloads are executed on mobile computing devices.

Non-limiting examples of how the workload can be optimized can include optimizing battery consumption of the computing system, bandwidth associated with the computing system, computing resource consumption associated with the computing system, and/or speed of execution of the workload by the computing system, among others. For example, if the computing system is a mobile computing device (e.g. a smartphone, IoT device, etc.), battery power of the computing device may be rapidly depleted when the workload is executed involving certain types of high power consumption memory devices. Accordingly, in order to optimize battery power consumption, for example of a mobile computing device, the hardware circuitry can cause at least a portion of the data corresponding to the workload to be written to a memory device that is characterized by a lower power consumption in executing the workload.

Another non-limiting example of the workload can be optimized can include optimizing execution of the workload by utilizing memory devices and/or media types that exhibit different memory capacities versus bandwidth capabilities. For example, a memory device that exhibits high capacity but low bandwidth (e.g., a NAND memory device) can be utilized for execution of some types of workloads (or portions thereof) while a memory device that exhibits high bandwidth but low capacity (e.g., a 3D stacked SDRAM memory device) can be utilized for execution of some types of workloads (or portions thereof). By leveraging the capacity of a memory device that exhibits high capacity but low bandwidth, or vice versa, for differing workloads, embodiments herein can optimize an amount of time, processing resources, and/or power consumed in executing resource intensive applications in a computing device or mobile computing device. Embodiments are not so limited, however, and other examples of optimizing execution of the workload in accordance with the disclosure are described in more detail, herein.

As described in more detail, herein, embodiments can further optimize execution of workloads in mobile computing system by writing data associated with the workloads to the memory devices based on characteristics of that data such as access frequencies of data involved in execution of the workloads. Access frequency of the data can refer to a quantity of accesses (e.g., reads, writes, etc.) involving the data in execution of the workloads. Access frequency of the data can be referred to herein in terms of "hot data" and "cold data." "Cold data," as used herein, means that a particular memory object has not been accessed for a long duration relative to other memory objects read from a memory device. "Hot data," as used herein, means that a particular memory object has been accessed frequently relative to other memory objects read from a memory device.

For example, if certain data involved in execution of a workload is determined to be "hot," such data can be written to a memory device that includes a media type that is well suited for making data quickly accessible. A non-limiting example of a memory device to which hot data can be written during execution of the workloads described herein is a volatile memory device such as a DRAM device.

In contrast, if certain data involved in execution of a workload is determined to be "cold," such data can be written to a memory device that includes a media type that is well suited for storing data that is not frequently accessed. A non-limiting example of a memory device to which cold data can be written during execution of the workloads described herein is a non-volatile memory device such as a NAND flash device.

In the following detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and structural changes may be made without departing from the scope of the present disclosure.

As used herein, designators such as "N," "M," etc., particularly with respect to reference numerals in the drawings, indicate that a number of the particular feature so designated can be included. It is also to be understood that the terminology used herein is for the purpose of describing particular embodiments only, and is not intended to be limiting. As used herein, the singular forms "a," "an," and "the" can include both singular and plural referents, unless the context clearly dictates otherwise. In addition, "a number of," "at least one," and "one or more" (e.g., a number of memory banks) can refer to one or more memory banks, whereas a "plurality of" is intended to refer to more than one of such things.

Furthermore, the words "can" and "may" are used throughout this application in a permissive sense (i.e., having the potential to, being able to), not in a mandatory sense (i.e., must). The term "include," and derivations thereof, means "including, but not limited to." The terms "coupled" and "coupling" mean to be directly or indirectly connected physically or for access to and movement (transmission) of commands and/or data, as appropriate to the context. The terms "data" and "data values" are used interchangeably herein and can have the same meaning, as appropriate to the context.

The figures herein follow a numbering convention in which the first digit or digits correspond to the figure number and the remaining digits identify an element or component in the figure. Similar elements or components between different figures may be identified by the use of similar digits. For example, 104 may reference element "04" in FIG. 1, and a similar element may be referenced as 204 in FIG. 2. A group or plurality of similar elements or components may generally be referred to herein with a single element number. For example, a plurality of reference elements, e.g., elements 544-1 to 544-N (or, in the alternative, 544-1, . . . 544-N) may be referred to generally as 544. As will be appreciated, elements shown in the various embodiments herein can be added, exchanged, and/or eliminated so as to provide a number of additional embodiments of the present disclosure. In addition, the proportion and/or the relative scale of the elements provided in the figures are intended to illustrate certain embodiments of the present disclosure and should not be taken in a limiting sense.

FIG. 1 is a functional block diagram in the form of a computing system 100 including an apparatus including a host 102 and a memory system 104 in accordance with a number of embodiments of the present disclosure. As used herein, an "apparatus" can refer to, but is not limited to, any of a variety of structures or combinations of structures, such as a circuit or circuitry, a die or dice, a module or modules, a device or devices, or a system or systems, for example. In some embodiments, the computing system 100 can be a mobile computing system (e.g., a mobile computing device, such as the mobile computing device 501 illustrated in FIG. 5, which can be a smartphone, a tablet, a phablet, and/or a IoT device, among others). The memory system 104 can include a number of different memory devices 123, 125 (and/or 227 illustrated in FIG. 2, herein), which can include one or more different media types 123, 125 (and/or 227 illustrated in FIG. 2, herein). The different memory devices 123, 125, and/or 227 can include one or more memory modules (e.g., single in-line memory modules, dual in-line memory modules, etc.).

The memory system 104 can include volatile memory and/or non-volatile memory. In a number of embodiments, memory system 104 can include a multi-chip device. A multi-chip device can include a number of different memory devices 123, 125, and/or 227, which can include a number of different memory types and/or memory modules. For example, a memory system can include non-volatile or volatile memory on any type of a module. As shown in FIG. 1, the computing system 100 can include a controller 120, which can include a processor 122. Each of the components (e.g., the host 102, the controller 120, the processor 122, and/or the memory devices 123, 125 can be separately referred to herein as an "apparatus."

The memory system 104 can provide main memory for the computing system 100 or could be used as additional memory and/or storage throughout the computing system 100. The memory system 104 can include one or more memory devices 123, 125, which can include volatile and/or non-volatile memory cells. At least one of the memory devices 123, 125 can be a flash array with a NAND architecture, for example. Further, at least one of the memory devices 123, 125 can be a dynamic random-access array of memory cells. Embodiments are not limited to a particular type of memory device. For instance, the memory system 104 can include RAM, ROM, DRAM, SDRAM, PCRAM, RRAM, and/or flash memory (e.g., NAND and/or NOR flash memory devices), among others.

Embodiments are not so limited, however, and the memory system 104 can include other non-volatile memory devices 123, 125 such as non-volatile random-access memory devices (e.g., NVRAM, ReRAM, FeRAM, MRAM, PCM), "emerging" memory devices such as resistance variable (e.g., 3-D Crosspoint (3D XP)) memory devices, memory devices that include an array of self-selecting memory (SSM) cells, memory devices that operate according to a compute express link (CXL) protocol, etc., or any combination thereof.

Resistance variable memory devices can perform bit storage based on a change of bulk resistance, in conjunction with a stackable cross-gridded data access array. Additionally, in contrast to many flash-based memories, resistance variable non-volatile memory can perform a write in-place operation, where a non-volatile memory cell can be programmed without the non-volatile memory cell being previously erased. In contrast to flash-based memories and resistance variable memories, self-selecting memory cells can include memory cells that have a single chalcogenide material that serves as both the switch and storage element for the memory cell.

In some embodiments, the memory system 104 can be a Compute Express Link (CXL) compliant memory system (e.g., the memory system can include a PCIe/CXL interface). CXL is a high-speed central processor (CPU)-to-device and CPU-to-memory interconnect designed to accelerate next-generation data center performance. CXL technology maintains memory coherency between the CPU memory space and memory on attached devices, which allows resource sharing for higher performance, reduced software stack complexity, and lower overall system cost.

CXL is designed to be an industry open standard interface for high-speed communications, as accelerators are increasingly used to complement CPUs in support of emerging applications such as artificial intelligence and machine learning. CXL technology is built on the peripheral component interconnect express (PCIe) infrastructure, leveraging PCIe physical and electrical interfaces to provide advanced protocol in areas such as input/output (I/O) protocol, memory protocol (e.g., initially allowing a host to share memory with an accelerator), and coherency interface. In some embodiments, the CXL technology can include a plurality of I/O lanes configured to transfer the plurality of commands to or from circuitry external to the memory controller at a rate of around thirty-two (32) giga-transfers per second. In another embodiments, the CXL technology can comprise a peripheral component interconnect express (PCIe) 5.0 interface coupled to a plurality of I/O lanes, wherein the memory controller is to receive commands involving at least one of a memory device, a second memory device, or any combination thereof, via the PCIe 5.0 interface according to a compute express link memory system.

As shown in FIG. 1, the memory devices 123, 125 include different types of memory devices. For example, the memory device 125 can be a non-volatile memory device, such as a resistance variable memory device, a memory device that operates according to the CXL protocol, a 3D XP memory device, or a NAND memory device, among others, and the memory device 123 can be a volatile memory device, such as a DRAM device, or vice versa. That is, the memory devices 123, 125 can include different media types 124, 126. Embodiments are not so limited, however, and the memory devices 123, 125 can include any type of memory devices provided that at least two of the memory devices 123, 125 include different media types 124, 126. As used herein, a "media type" generally refers to a type of memory cell architecture that corresponds to the memory devices 123, 125. For example, one of the media types 124, 126 can correspond to an array of memory cells that includes at least one capacitor and at least one transistor, while another of the media types 124, 126 can include an array of floating-gate metal-oxide-semiconductor field-effect transistors. In some embodiments, at least one of the media types 124, 126 can include an array of resistance variable memory cells that are configured to perform bit storage based on a change in a bulk resistance associated with the resistance variable memory cells.

As illustrated in FIG. 1, a host 102 can be coupled to the memory system 104. In a number of embodiments, the memory system 104 can be coupled to the host 102 via one or more channels (e.g., channel 103). In FIG. 1, the memory system 104 is coupled to the host 102 via channel 103, which can, in addition, be coupled to the controller 120 and/or the processor 122 of the memory system 104. The controller 120 and/or the processor 122 are coupled to the memory devices 123, 125 via channel(s) 105, 107. In some embodiments, each of the memory devices 123, 125 are coupled to the controller 120 and/or the processor 122 by one or more respective channels 105, 107 such that each of the memory devices 123, 125 can receive messages, commands, requests, protocols, or other signaling that is compliant with the type of memory device 123, 125 (e.g., messages, commands, requests, protocols, or other signaling that is compliant with the media type 124, 126 of the memory devices 123, 125) coupled to the controller 120.

The computing system 100 can further include an imaging device 121. The imaging device 121 can be communicatively coupled to the host 102 and/or to the memory device 104 (e.g., to the controller 120 and/or the processor 122). The imaging device 121 can be a camera, sonography device, ultrasound device, stereoscopic imaging device, magnetic resonance imaging device, infrared imaging device, or other imaging device that can capture data that includes images or streams of images (e.g., streaming video and/or "live-streaming video") in real-time and transmit information corresponding to the images and/or streams of images to the computing system 100. In general, the imaging device can be any mechanical, digital, or electronic imaging device; still camera; camcorder; motion picture camera; or any other instrument, equipment, or format capable of recording, storing, or transmitting images, video, and/or information.

As used herein, the term "live-streaming video," and variants thereof, generally refers to sequences of images that are concurrently (or nearly concurrently) captured and processed, reproduced, and/or broadcasted. In some embodiments, "live-streaming" video can be referred to in the alternative herein as "data captured by an imaging device" or "data captured from an imaging device." Further, as used herein, the term "streaming video," and variants thereof generally refers to sequences of images that are captured by an imaging device and subsequently processed, reproduced, and/or broadcasted. In some embodiments, "streaming" video can be referred to in the alternative herein as "data captured by an imaging device" or "data captured from an imaging device."

Generally, such data (e.g., images, streams of images and/or or "live-streaming" video) captured by the imaging device can be displayed or broadcast on a viewing device and/or processed by a processor within a threshold period of time after capture by the imaging device. In some embodiments, the data captured by the imaging device can be displayed, broadcast, and/or processed within a threshold period of time relative to capture of the imaging device that is on the order of seconds or minutes, as opposed to hours or days. These data (e.g., streams of images and/or video) can include any media content live or recorded that is delivered to or by a computing system, such as a mobile computing device, via a connection path, such as a wired communication channel, and/or a non-wired communication channel such as the internet and displayed or broadcast in real time. Accordingly, as described in more detail herein, data (e.g., images of blood cells) can be captured by an imaging device and then stored in memory coupled to the imaging device, processed by a processor associated with the memory device, and subsequently broadcast and/or the data can be captured by the imaging device, stored in memory coupled to the imaging device, processed by a processor associated with the memory device, and/or broadcast in real-time (or near real-time based on latencies in transmission between various components described herein) as the data is captured by the imaging device.

In some embodiments, the imaging device 121 can capture data, such as images and/or streaming video (e.g., live-streaming video) that includes images used in a medical self-diagnostic test. As used herein, a "medical self-diagnostic test" generally refers to medical testing performed by a patient from a location different than a doctor's office, clinic, hospital, or other health care service location. In general, a medical self-diagnostic test is performed by a patient using equipment (e.g., a mobile computing device in some embodiments of the disclosure) that is owned by the patient and is commonly not medical grade equipment. For example, embodiments herein described the use of a smartphone or other mobile computing device in performance of a medical self-diagnostic test. In at least one embodiment, the medical self-diagnostic test can include execution of an application to perform a blood imaging operation or technique.

In some embodiments, the images and/or steaming video captured by the imaging device 121 can include images and/or streaming video of blood (e.g., blood vessels) flowing through one or more blood veins, among others. Such images and/or streaming video can be captured by the imaging device 121 and processed locally within the memory system 104 as part of a medical self-diagnostic test to, for example, detect and/or analyze abnormalities in the blood. By utilizing aspects of the disclosure, such medical self-diagnostic tests can be performed in the absence of a visit to a doctor or hospital, which can alleviate wait times for medical patients and/or can preemptively capture medical information for a medical professional to view at a later time. In addition, such medical self-diagnostic tests can provide information over time in the absence of doctor office visits that can be amalgamated over time to assist in early detection of medical issues and/or to generate a consistent record of medical abnormalities that can later be analyzed by a doctor or other clinical professional.

For example, magnetic resonance images or other large, detailed, high bandwidth images and/or video of blood (e.g., blood vessels) within a blood vein can be captured by the imaging device 121 and processed by the memory system 104 to detect, monitor, or otherwise analyze characteristics of the blood to determine if any abnormalities are present with respect to the blood in the absence of visits to a doctor's office or hospital. This can allow for early detection and monitoring or abnormalities of the blood to create a consistent record of blood health to assist in early detection and treatment of various diseases.

Traditionally, capture and processing/analysis of such medical abnormalities is a highly specialized and computing resource intensive process. For example, applications and hence, the workloads corresponding thereto, to perform medical imaging and/or process medical imaging data can be extremely computing resource intensive. One reason for this is that the level of detail captured in images or video for medical imaging purposes is often times extremely detailed and therefore memory resource intensive (e.g., because of the detail captured in such images and/or videos, the file sizes corresponding to the images and/or videos can be relatively large in comparison to, for example, a simple photograph). Another reason for the resource intensive nature of execution of applications and corresponding workloads to process medical imaging data is that the detail and size of the data (e.g., the file sizes associated with medical imaging data) can require multiple resource intensive operations in processing.

However, embodiments herein can allow for selective processing of workloads involving images and/or video corresponding to the images and/or video captured by the imaging device 121 such that the captured imaging data and/or the workloads corresponding to execution of applications involving the same are allocated to the memory devices 123, 125, 227 to optimize the performance of the memory system 104 such that the medical self-diagnostic tests described herein can be realized using a mobile computing device, such as a smartphone, among other mobile computing devices described herein.

In some embodiments, the images and/or video captured by the imaging device 121 and processed by the memory system 104 can be uploaded or otherwise transferred to a medical professional to assist in building long term records of the development of potential medical abnormalities and providing notifications of these records to a medical professional even if a patient is remiss in visiting a doctor or hospital regularly.

The host 102 can be a host system such as a personal laptop computer, a desktop computer, a digital camera, a smart phone, a memory card reader, and/or an internet-of-things (IoT) enabled device, among various other types of hosts. In some embodiments, however, the host 102 is a mobile computing device such as a digital camera, a smart phone, a memory card reader, and/or an internet-of-things (IoT) enabled device, among various other types of hosts (e.g., in some embodiments, the host 102 is not a personal laptop computer or desktop computer). The host 102 can include a system motherboard and/or backplane and can include a memory access device, e.g., a processor (or processing device).

One of ordinary skill in the art will appreciate that "a processor" can intend one or more processors, such as a parallel processing system, a number of coprocessors, etc. The system 100 can include separate integrated circuits or one or more of the host 102, the memory system 104, the control circuitry 120, and/or the memory devices 123, 125 can be on the same integrated circuit. The computing system 100 can be, for instance, a server system and/or a high-performance computing (HPC) system and/or a portion thereof. Although the example shown in FIG. 1 illustrate a system having a Von Neumann architecture, embodiments of the present disclosure can be implemented in non-Von Neumann architectures, which may not include one or more components (e.g., CPU, ALU, etc.) often associated with a Von Neumann architecture.

The memory system 104 can include a controller 120, which can include a processor 122. The processor 122 can be provided in the form of an integrated circuit, such as an application-specific integrated circuit (ASIC), field programmable gate array (FPGA), reduced instruction set computing device (RISC), advanced RISC machine, system-on-a-chip, or other combination of hardware and/or circuitry that is configured to perform operations described in more detail, herein. In some embodiments, the processor 122 can comprise one or more processors (e.g., processing device(s), co-processors, etc.)

The processor 122 can perform operations to monitor and/or determine characteristics of workloads running on the memory system 104. The characteristics can include information such as bandwidth consumption, memory resource consumption, access frequency (e.g., whether the data is hot or cold), and/or power consumption in execution of the workloads, among others. The processor 122 can control writing of at least a portion of the data to a different memory device 123, 125 in order to optimize execution of the workload, balance the workload between different memory devices 123, 125 for media management purposes, and/or optimize battery consumption of the computing system 100, among others.

In a non-limiting example, an apparatus (e.g., the computing system 100) can include a first memory device 123 comprising a first type of media 124 and a second memory device 125 comprising a second type of media 126. The first memory device 123, the second memory device 125, and the processor 122 can, in some embodiments, be resident on a mobile computing device (e.g., the mobile computing device 501 illustrated in FIG. 5, herein) such as a smartphone or other mobile computing device. A processor 122 can be coupled to the first memory device 123 and the second memory device 125. The processor 122 can receive information captured by an imaging device 121 couplable to the processor 122.

As used herein, the term "resident on" refers to something that is physically located on a particular component. For example, the first memory device 123, the second memory device 125, and/or the processor 122 can, in some embodiments, being resident on a smartphone (e.g., the computing device 100 and/or the mobile computing device 501 illustrated in FIG. 5, herein) refers to a condition in which the first memory device 123, the second memory device 125, and/or the processor 122 is physically coupled to, or physically within, smartphone (e.g., the computing device 100 and/or the mobile computing device 501 illustrated in FIG. 5, herein). The term "resident on" may be used interchangeably with other terms such as "deployed on" or "located on," herein.

In this example, the processor 122 can receive an application initiation indicator. The application initiation indicator can include signals, commands, instructions, or the like, that indicate to the processor 122 that an application to perform a medical self-testing operation (e.g., an operation to detect an abnormality in blood, such as the blood cells 544, 546 illustrated in FIG. 5, herein) is to be executed. In some embodiments, the application initiation indicator can include signals, commands, instructions, or the like that indicate to the processor 122 that images and/or video that contain greater than a threshold quantity of pixels, greater than a threshold file size, greater than a threshold image resolution, etc. will be received by the processor 122 and/or the memory system 104.

The processor 122 can reallocate computing resources among the first memory device 123 and the second memory device 125 based, at least in part, on determined characteristics of the first memory device 123 and the second memory device 125 in response to receipt of the application initiation indicator. The processor 122 can determine the characteristics of the first memory device 123 and the second memory device 125 prior to, or during, execution of the application. In some embodiments, the determined characteristics of the first memory device 123 and the second memory device 125 can include a bandwidth, a memory access time, a latency, and/or a memory cell density, among other characteristics, of the first memory device 123 and the second memory device 125.

The processor 122 can receive data captured by an imaging device 121. As described in more detail, herein, the data can include images and/or video of blood cells to be analyzed as part of execution of an application to detect an abnormality in the blood cells. In some embodiments, the processor 122, the imaging device 121, the first memory device 123, and the second memory device 125 are resident on a mobile computing device (e.g., the mobile computing device 501 illustrated in FIG. 5, herein). In such embodiments, the processor 122 can receive images of blood flow in a blood vein (e.g., the blood vein 542 illustrated in FIG. 5, herein) as part of the data captured by the imaging device 121 and execute the application to determine whether an abnormality is detected in the received images of the blood flow.

The processor 122 can write the data captured by the imaging device 121 to the first memory device 123 or the second memory device 125 based on the determined characteristics for the first memory device 123 and the second memory device 125. After the processor 122 has written the data to the first memory device 123 or the second memory device 125, the processor 122 can execute the application while the data captured by the imaging device 121 is written to the first memory device 123 or the second memory device 125.

For example, in some embodiments, the processor 122 can process the received information captured by the imaging device 121. In some embodiments, the operation to process received information captured by the imaging device 121 can involve an application having a particular workload corresponding thereto. The processor 122 can determine characteristics of the workload when the workload is written to the first memory device 123 or the second memory device 125. In some embodiments, the characteristics of the workload can include at least one of an access frequency of data associated with the workload, a latency associated with execution of the workload, and/or an amount of processing resources consumed in execution of the workload. In some embodiments, the application and/or the workload can involve processing of data received and/or captured by the imaging device 121.

The processor 122 can determine, based on the characteristics of the workload, whether to write at least a portion of data associated with the workload to the other of the first memory device 123 or the second memory device 125 and control allocation of execution of the workload that is written to the other of the first memory device 123 or the second memory device 125 such that at least the portion of the workload is subsequently executed after at least the portion of the workload has been written to the other of the first memory device 123 or the second memory device 125. In some embodiments, the subsequently executed workload can involve processing of data received and/or captured by the imaging device 121.

In some embodiments, the processor 122 can determine that the application initiation indicator corresponds to execution of an application to process data captured by the imaging device that exceeds a threshold quantity of pixels and/or determine the characteristics of the first memory device 123 and the second memory device 125. The processor 122 can, in some embodiments, cause performance of the operation to process the image or the video by replacing at least one pixel of the image or the video, correcting a blurred portion of the image or the video, or removing noise from the image and/or the video. For example, in the process of image capture, one or more pixels of an image or video may become corrupted, which can cause the image to be distorted, blurred, or include other types of noise. By performing operations to replace the corrupted portions (e.g., pixels) of the image, the image or video quality can be recovered and/or improved using circuitry that is entirely resident on the memory system (e.g., in the absence of transferring the images and/or video to external circuitry, such as the host 102). In some embodiments, the image and/or the video can be received from the imaging device 121 and processed in a live-streaming manner. For example, the video can be a live video captured in real-time by the imaging device 121 and written in real time to the memory system 104.

As mentioned above, the first memory device 123 or the second memory device 125 can be a non-persistent (e.g., volatile) memory device, and the other of the first memory device 123 or the second memory device 125 can be a persistent (e.g., non-volatile) memory device. In addition, as mentioned above, in some embodiments, the first type of memory or the second type of memory, or both, comprises sets of memory cells that exhibit different storage characteristics. For example, the first memory device 123 can have a first media type 124 and the second memory device 125 can have a second media type 126 associated therewith.

Figure 3:
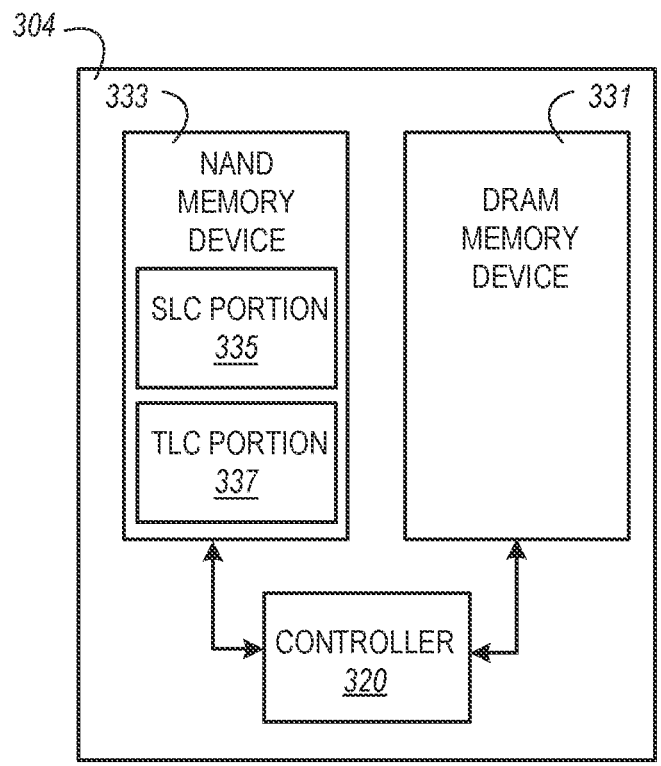
FIG. 3 is a functional block diagram in the form of an apparatus including a memory system in accordance with a number of embodiments of the present disclosure.
Figure 4:
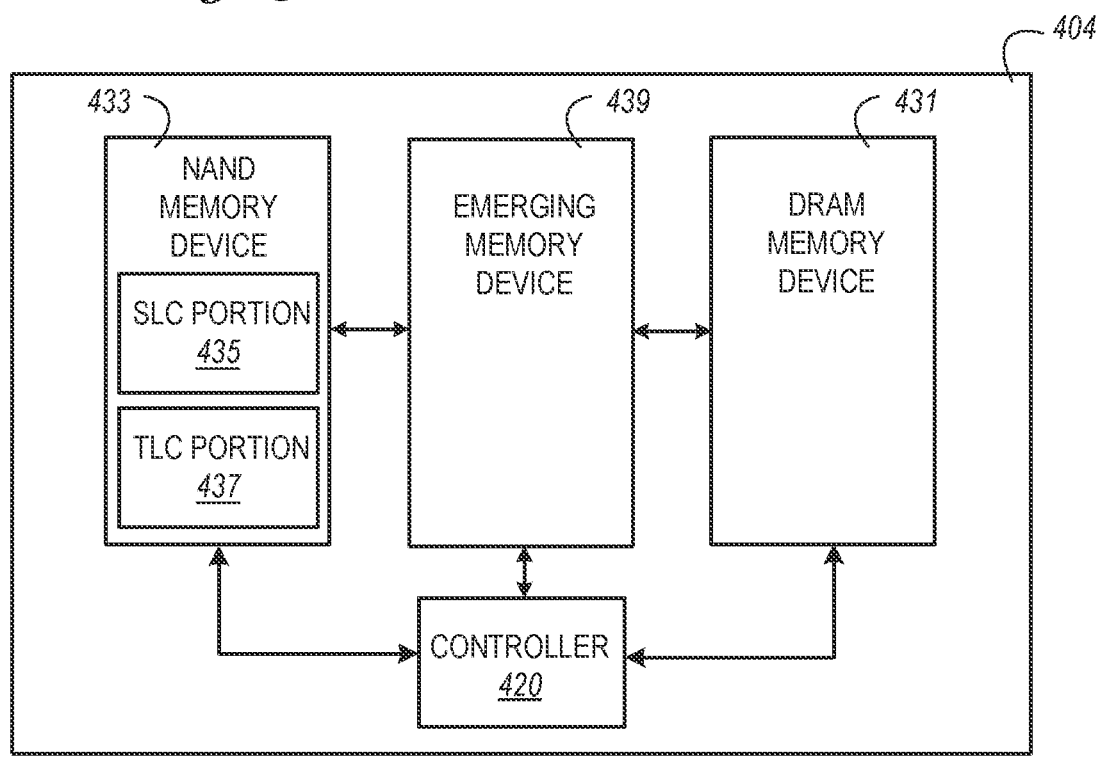
FIG. 4 is another functional block diagram in the form of an apparatus including a memory system in accordance with a number of embodiments of the present disclosure.

Continuing with the above non-limiting example, the first memory device 123 or the second memory device 125 can be a NAND flash memory device that comprises a set of single level memory cells (SLCs) and a set of multi-level memory cells (MLCs), as shown in FIGS. 3 and 4, herein. In such embodiments, the processor 122 can write at least the portion of the data associated with the workload to the set of SLC memory cells or the set of MLC memory cells based, at least in part, on receipt of the application initiation indicator. In some embodiments, the set of SLCs can be configured to store a look-up table to facilitate writing of at least the portion of the data to the other of the first memory device 123 or the second memory device 125.

As used herein, the term "look-up table" generally refers to a data structure that contains indexing information that can correspond to desired output formats of data written to the memory system 104. For example, the look-up table can include pre-fetched information that can be used by the memory system 104 to output various types of data processed by the memory system in a requested format. In some embodiments, the look-up table can be included in a flash memory device, such as the NAND memory device 333, for example, in the SLC portion 335 of the NAND memory device 333. The look-up table can store data corresponding to artificial intelligence and/or machine learning applications. In such embodiments, it may be beneficial to store the look-up table in a SLC portion of the memory device, as SLC memory generally offers high access speeds and accurate storage. In some embodiments, such artificial intelligence and/or machine learning applications can be executed in connection with performance of the operations described herein.

The embodiment of FIG. 1 can include additional circuitry that is not illustrated so as not to obscure embodiments of the present disclosure. For example, the memory system 104 can include address circuitry to latch address signals provided over I/O connections through I/O circuitry. Address signals can be received and decoded by a row decoder and a column decoder to access the memory system 104 and/or the memory devices 123, 125. It will be appreciated by those skilled in the art that the number of address input connections can depend on the density and architecture of the memory system 104 and/or the memory devices 123, 125.

Figure 2:
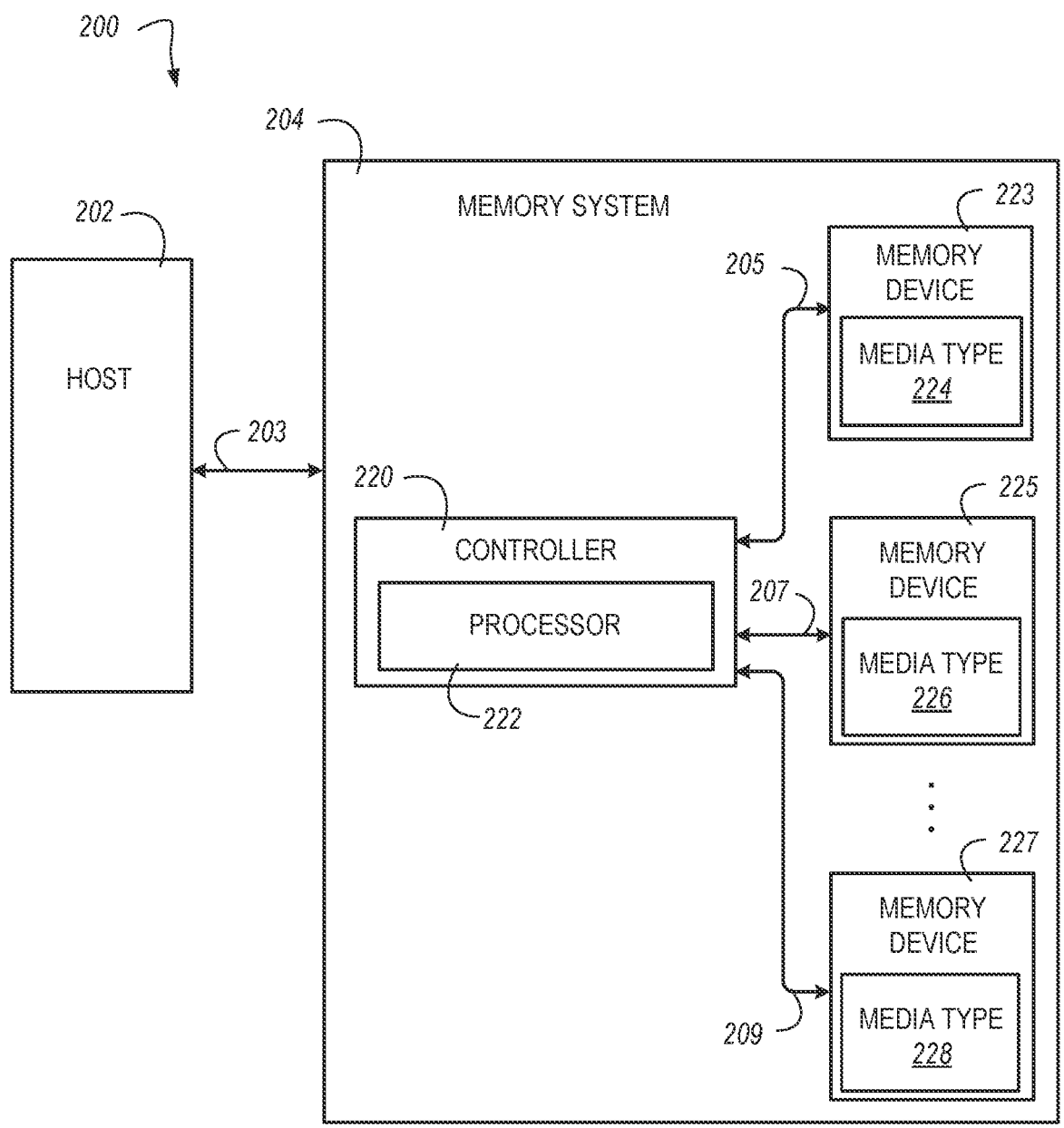
FIG. 2 is another functional block diagram in the form of a computing system including an apparatus including a host and a memory system in accordance with a number of embodiments of the present disclosure.

FIG. 2 is another functional block diagram in the form of a computing system 200 including an apparatus including a host 202 and a memory system 204 in accordance with a number of embodiments of the present disclosure. In some embodiments, the computing system 200 can be a mobile computing system (e.g., a mobile computing device 501, such as a smartphone, a tablet, a phablet, and/or a IoT device, among others). The memory system 204 can include a number of different memory devices 223, 225, 227, which can include one or more different media types 223, 225, 227. The different memory devices 223, 225, and/or 227 can include one or more memory modules (e.g., single in-line memory modules, dual in-line memory modules, etc.). The host 202, memory system 204, controller 220, processor 222, memory devices 223, 225 and/or the media types 224, 226 can be analogous to the host 102, memory system 104, controller 120, processor 122, memory devices 123, 125 and/or the media types 124, 126 illustrated in FIG. 1, herein.

In some embodiments, each of the memory devices 223, 225, and 227 can be a different type of memory device. Accordingly, in some embodiments, each of the memory devices 223, 225, and 227 can include different media types 224, 226, and 228. In a non-limiting example, the memory device 223 can be a volatile memory device, such as a DRAM device and can include a media type 224 that corresponds to a DRAM memory device (e.g., an array of memory cells that include at least one capacitor and at least one transistor). Continuing with this example, the memory device 225 can be a flash memory device, such as a NAND memory device and can include a media type 226 that corresponds to a NAND memory device (e.g., comprises an array of floating-gate metal-oxide-semiconductor field-effect transistors). In this non-limiting example, the memory device 227 can be an emerging memory device (e.g., the emerging memory device 439 illustrated in FIG. 4, herein), such as the emerging memory devices described above, and can include a media type 228 that corresponds to an emerging memory device (e.g., an array of resistance variable memory cells that are configured to perform bit storage based on a change in a bulk resistance associated with the resistance variable memory cells, an array of self-selecting memory cells, an array of memory cells that operate according to the CXL protocol, etc.).

The memory devices 223, 225, and 227 can be configured to read, write, and/or store data, such as the images of blood described herein, corresponding to one or more workloads executed by the computing system 200. An application corresponding to the workload can be executed by, for example, the processor 222 to cause the data to be written to the memory devices 223, 225, and 227 to be used in execution of the application and/or workload. As described above, the controller 220 can control writing at least a portion of the data to a different memory device than the memory device in which the data is initially written based on characteristics of the workload.

For example, if data corresponding to a particular workload is stored in the memory device 223, the controller 220 and/or the processor 222 can, in response to a determination that the workload may be more efficiently executed (e.g., optimized) using a different memory device, cause at least a portion of the data corresponding to the particular workload to be written to the memory device 225 and/or to the memory device 227.

Figure 5:
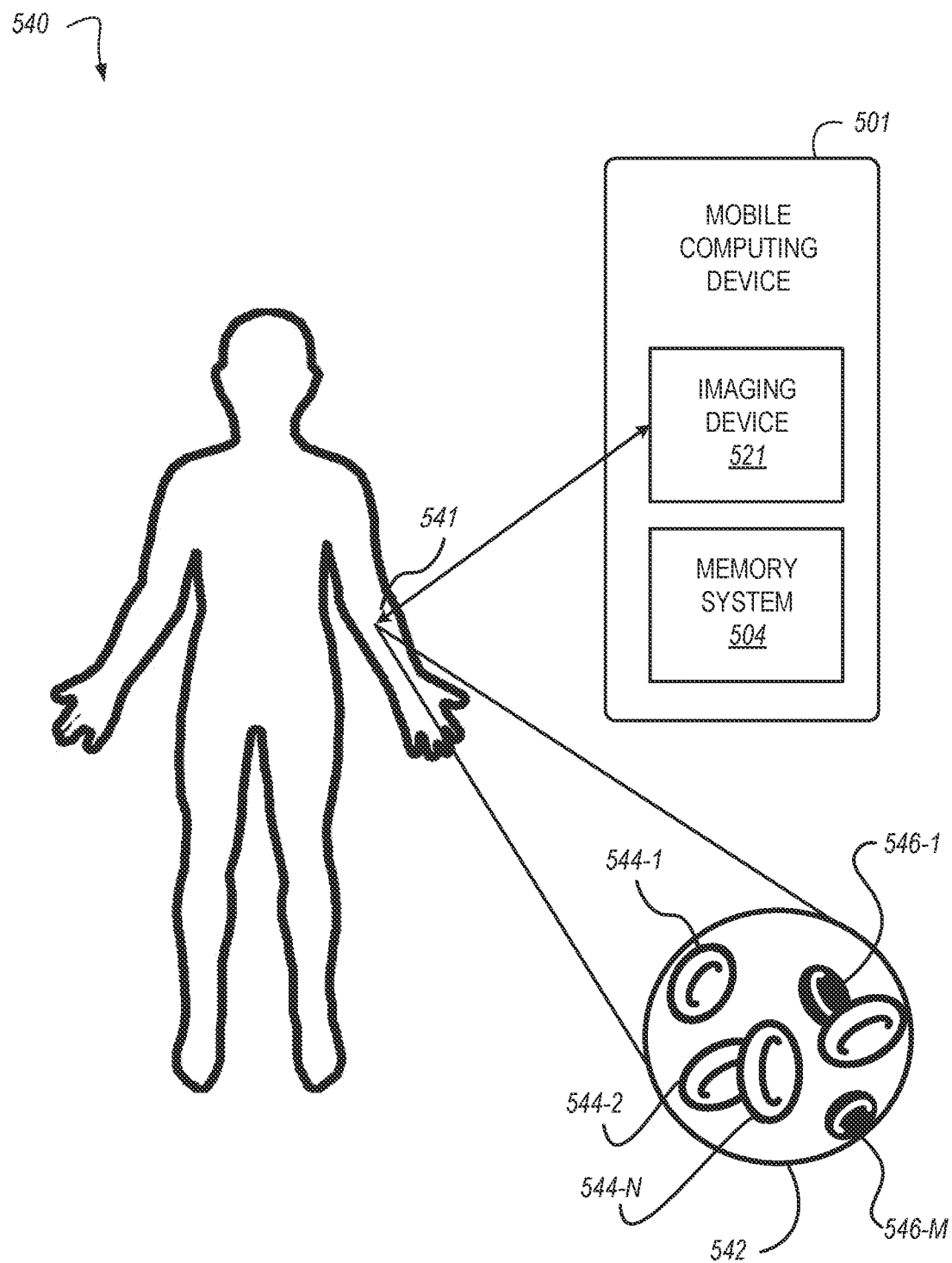
FIG. 5 is a diagram illustrating a human medical self-diagnostic test subject and a mobile computing device in accordance with a number of embodiments of the present disclosure.

In a non-limiting example, a system (e.g., the computing system 200 and/or the mobile computing device 501 illustrated in FIG. 5, herein) can include a memory system 204 comprising a processor 222, a first memory device 223 comprising a first type of media 224, a second memory device 225 comprising a second type of media 226, and a third memory device 227 comprising a third type of media 228. In some embodiments, the first memory device 223 can be a dynamic random-access memory device, the second memory device 225 can be a NAND flash memory device, and the third memory device 227 can be an emerging memory device, such as a CXL memory device, a 3D XP memory device, a self-selecting cell memory device, etc., as described above.

In at least one embodiment, the media type 224 comprises an array of memory cells that include at least one capacitor and at least one transistor, the media type 226 comprises an array of floating-gate metal-oxide-semiconductor field-effect transistors, and the type of media 228 comprises an array of resistance variable memory cells that are configured to perform bit storage based on a change in a bulk resistance associated with the resistance variable memory cells.

An imaging device (e.g., the imaging device 121 illustrated in FIG. 1, herein) can be coupled to the memory device 204. In such examples, the processor 222 can receive signaling comprising information captured by the imaging device and generate, based on characteristics of the one or more received images, an application initiation indicator corresponding to execution of an application corresponding to detection of an abnormality in at least a portion of a living creature, such as the human medical self-diagnostic test subject 540 illustrated in FIG. 5, herein.

The processor 222 can reallocate computing resources among the first memory device 223, the second memory device 225, or the third memory device 227, or any combination thereof based, at least in part, on characteristics of the first memory device 223, the second memory device 225, and the third memory device 227 in response to generation of the application initiation indicator. As described herein, the processor 222 can determine the characteristics of the first memory device 223, the second memory device 225, and the third memory device 227 prior to, or during, execution of the application, while the determined characteristics of the first memory device 223, the second memory device 225, and the third memory device 227 can include a bandwidth, a memory access time, a latency, a memory cell density, or any combination thereof, of the first memory device 223, the second memory device 225, and the third memory device 227. In some embodiments, the processor 222 can reallocate the computing resources such that greater than a threshold amount of computing resources are available to the memory device that exhibits characteristics that are consistent with processing and/or performing operations using the images captured by the imaging device.

The processor 222 can write at least a portion of the one or more images captured by the imaging device to the first memory device 223, the second memory device 225, or the third memory device 227, or combinations thereof in response to generation of the application initiation indicator. In some embodiments, the processor 222 can execute the application corresponding to detection of the abnormality in at least the portion of the living creature while the one or more images captured by the imaging device are written to the first memory device 223, the second memory device 225, or the third memory device 227, or any combination thereof.

As described herein, in some embodiments, the memory system 204 and the imaging device are resident on a mobile computing device (e.g., the mobile computing device 501 illustrated in FIG. 5, herein). In such embodiments, the processor 222 can cause results corresponding to execution of the application to detect the abnormality in at least the portion of the living creature to be transferred to a hospital, a doctor's office, or an emergency service provider, or any combination thereof. Embodiments are not so limited, however, and in some embodiments, the mobile computing device can include a display screen and the processor 222 can generate dietary recommendations based, at least in part, on results of execution of the application to detect the abnormality in at least the portion of the living creature and display the dietary recommendations on the display screen.

Continuing with this example, in embodiments in which the memory system 204 and the imaging device are resident on a mobile computing device, the processor 222 can execute one or more sets of machine learning instructions to determine the characteristics of the first memory device 223, the second memory device 225, and the third memory device 227 based, at least in part, on monitored benchmark data associated with the first memory device 223, the second memory device 225, and the third memory device 227. As used herein, the term "benchmark data" generally refers to data that can be used to test characteristics of a memory device 204, such as read/write speed, throughput, bandwidth, accuracy, and/or data retention, among other test data that indicates the overall performance of the memory device 204. In such embodiments, the processor 222 can reallocate the computing resources among the first memory device 223, the second memory device 225, or the third memory device 227, or any combination thereof based, at least in part, on the determined characteristics of the first memory device 223, the second memory device 225, and the third memory device 227.

In some embodiments in which the memory system 204 and the imaging device are resident on a mobile computing device, the processor 222 can determine characteristics of the one or more received images based on images previously captured by the imaging device and generate the application initiation indicator based on the determined characteristics of the one or more images. For example, the processor 222 can determine that images captured by the imaging device are similar to images previously captured by the imaging device and determine that an application corresponding to processing the newly captured images is likely to be executed based on past execution of such an application in response to receipt of similar images.

As described herein, the memory system 204 and the imaging device can be resident on a mobile computing device and the processor 222 can receive data (e.g., images, streams of images, and/or live-streaming information) from the imaging device in conjunction with performance of a medical self-diagnostic test and the processor 222 can write at least a portion of the data from the imaging device to at least one of the other of the memory device 223, the memory device 225, or the memory device based 227, at least on part, on a determined category associated with the medical self-diagnostic test. In this example, the processor 222 can execute, using at least the portion of the data captured by the imaging device written to the memory device 223, the memory device 225, or the memory device 227, a workload that includes at least the portion of the data captured from the imaging device.

In such examples, the processor 222 can determine the characteristics of the executed workload while the data is written to the memory device 223, the memory device 225, or the memory device 227 by monitoring at least one of an access frequency of data associated with the workload, a latency associated with execution of the workload, and/or an amount of processing resources consumed in execution of the workload and write at least the portion of data associated with the workload to at least one of the other of the memory device 223, the memory device 225, or the memory device 227 based, at least on part, on the determined access frequency of data associated with the workload, the latency associated with execution of the workload, and/or the amount of processing resources consumed in execution of the workload.

In some embodiments, at least a portion of the data written to the memory device 223, the memory device 225, or the memory device 227 is formatted according to a universal number format or a posit format. In contrast to the IEEE 754 floating-point or fixed-point binary formats, which include a sign bit sub-set, a mantissa bit sub-set, and an exponent bit sub-set, universal number formats, such as posits include a sign bit sub-set, a regime bit sub-set, a mantissa bit sub-set, and an exponent bit sub-set. This can allow for the accuracy, precision, and/or the dynamic range of a posit to be greater than that of a float, or other numerical formats. In addition, posits can reduce or eliminate the overflow, underflow, NaN, and/or other corner cases that are associated with floats and other numerical formats. Further, the use of posits can allow for a numerical value (e.g., a number) to be represented using fewer bits in comparison to floats or other numerical formats.

As used herein, a "precision" refers to a quantity of bits in a bit string that are used for performing computations using the bit string. For example, if each bit in a 16-bit bit string is used in performing computations using the bit string, the bit string can be referred to as having a precision of 16 bits. However, if only 8-bits of a 16-bit bit string are used in performing computations using the bit string (e.g., if the leading 8 bits of the bit string are zeros), the bit string can be referred to as having a precision of 8-bits. As the precision of the bit string is increased, computations can be performed to a higher degree of accuracy. Conversely, as the precision of the bit string is decreased, computations can be performed using to a lower degree of accuracy. For example, an 8-bit bit string can correspond to a data range consisting of two hundred and fifty-five (256) precision steps, while a 16-bit bit string can correspond to a data range consisting of sixty-five thousand five hundred and thirty-six (63,536) precision steps.

As used herein, a "dynamic range" or "dynamic range of data" refers to a ratio between the largest and smallest values available for a bit string having a particular precision associated therewith. For example, the largest numerical value that can be represented by a bit string having a particular precision associated therewith can determine the dynamic range of the data format of the bit string. For a universal number (e.g., a posit) format bit string, the dynamic range can be determined by the numerical value of the exponent bit sub-set of the bit string.

A dynamic range and/or the precision can have a variable range threshold associated therewith. For example, the dynamic range of data can correspond to an application that uses the data and/or various computations that use the data. This may be due to the fact that the dynamic range desired for one application may be different than a dynamic range for a different application, and/or because some computations may require different dynamic ranges of data. Accordingly, embodiments herein can allow for the dynamic range of data to be altered to suit the requirements of disparate applications and/or computations. In contrast to approaches that do not allow for the dynamic range of the data to be manipulated to suit the requirements of different applications and/or computations, embodiments herein can improve resource usage and/or data precision by allowing for the dynamic range of the data to varied based on the application and/or computation for which the data will be used.

FIG. 3 is a functional block diagram in the form of an apparatus including a memory system 304 in accordance with a number of embodiments of the present disclosure. FIG. 3 illustrates a memory system 304, which can be analogous to the memory system 104 illustrated in FIG. 1 and/or the memory system 204 illustrated in FIG. 2, herein. As shown in FIG. 3, the memory system 304 includes a controller 320 (which can be analogous to the controller 120 illustrated in FIG. 1 and/or the controller 220 illustrated in FIG. 2, herein), a DRAM memory device 331 (which can be analogous to one of the memory devices 123, 125 illustrated in FIG. 1 and/or one of the memory devices 223, 225, 227 illustrated in FIG. 2, herein), and a NAND memory device 333 (which can be analogous to one of the memory devices 123, 125 illustrated in FIG. 1 and/or one of the memory devices 223, 225, 227 illustrated in FIG. 2, herein).

As shown in FIG. 3, the NAND memory device 333 can include various portions of memory cells, which can include a set of single level memory cells (SLCs) 335 and a set of multi-level memory cells (MLCs), such as a set of triple-level memory cells (TLCs) 337, quad-level cells (QLCs), etc. In some embodiments, the controller can cause at least a portion of data corresponding to an image or sequence of images, such as images of blood cells within a blood vein, used by an application to detect abnormalities in the blood that is executed on the memory system 304 to be written to the SLC portion 335 and/or or the TLC portion 337 based on the characteristics of the application (e.g., in response to receipt of an application initiation indicator) involving the data.

In some embodiments, data that is classified as hot data can be written to the SLC portion 335 while data that is classified as cold data can be written to the TLC portion 337, or vice versa, as part of optimizing performance of the memory system 304 during execution of the application and corresponding workloads. By selectively writing portions of data involved in execution of the application to different memory portions (e.g., to a SLC portion 335 and/or a TLC portion 337) of the NAND memory device 333, performance of the computing system, especially during execution of applications to detect abnormalities in blood described herein, can be improved in comparison to some approaches. Embodiments are not so limited, however, and in some embodiments, hot data can be written to the DRAM memory device, colder data can be written to the NAND memory device 333, and cold data can be written to the emerging memory device 339.

For example, by selectively writing portions of data that correspond to workloads that benefit from rapid executed to the DRAM memory device 331 while writing portions of data that correspond to execution of applications and workloads that may not benefit as much from rapid execution to the SLC portion 335 and/or the TLC portion 337, and/or to an emerging memory device (e.g., the emerging memory device 439 illustrated in FIG. 4), workloads can be allocated to memory devices within the memory system 304 that can allow for optimized execution of the workloads within the memory system 304 rapidly. For similar reasons, portions of the workloads can be written to an emerging memory device (e.g., the emerging memory device 439 illustrated in FIG. 4, herein).

In some embodiments, at least a portion of the SLC portion 335 of the NAND memory device 333 can be allocated for storage of a look-up table. The look-up table can be a data structure that contains indexing information that can correspond to desired output formats of data written to or from the memory system 304. For example, the look-up table can include pre-fetched information that can be used by the memory system 304 to output various types of data processed by the memory system 304 in a requested format. In some embodiments, the look-up table can facilitate writing of at least a portion of data involved in a workload to one of the memory devices described herein.

FIG. 4 is another functional block diagram in the form of an apparatus including a memory system 404 in accordance with a number of embodiments of the present disclosure. FIG. 4 illustrates a memory system 404, which can be analogous to the memory system 104 illustrated in FIG. 1, the memory system 204 illustrated in FIG. 2, and/or the memory system 304 illustrated in FIG. 3, herein.

As shown in FIG. 4, the memory system 404 includes a controller 420 (which can be analogous to the controller 120 illustrated in FIG. 1, the controller 220 illustrated in FIG. 2, and/or the controller 320 illustrated in FIG. 3, herein), a DRAM memory device 431 (which can be analogous to one of the memory devices 123, 125 illustrated in FIG. 1, one of the memory devices 223, 225, 227 illustrated in FIG. 2, and/or one of the DRAM memory device 331 illustrated in FIG. 3, herein), a NAND memory device 433 (which can be analogous to one of the memory devices 123, 125 illustrated in FIG. 1, one of the memory devices 223, 225, 227 illustrated in FIG. 2, and/or the NAND memory device 333 illustrated in FIG. 3, herein), and an emerging memory device 439 (which can be analogous to one of the memory devices 123, 125 illustrated in FIG. 1 and/or one of the memory devices 223, 225, 227 illustrated in FIG. 2, herein).

The DRAM memory device 431 can include an array of memory cells that include at least one transistor and one capacitor configured to store a charge corresponding to a single data bit. The NAND memory device 433 can include various portions of memory cells, which can include a set of single level memory cells (SLCs) 435 and a set of multi-level memory cells (MLCs), such as a set of triple-level memory cells (TLCs) 437, which can be analogous to the SLC portion 335 and the TLC portion 337, respectively, illustrated and described in connection with FIG. 3, herein.

The emerging memory device 439 can be an emerging memory device, as described above. For example, the emerging memory device 439 can be a resistance variable (e.g., 3-D Crosspoint (3D XP)) memory devices, memory devices that include an array of self-selecting memory (SSM) cells, memory devices that operate according to a CXL protocol, etc., or any combination thereof.

FIG. 5 is a diagram illustrating a human medical self-diagnostic test subject 540 and a mobile computing device 501 in accordance with a number of embodiments of the present disclosure. As shown in FIG. 5, the mobile computing device 501 includes an imaging device 521, which can be analogous to the imaging device 121 illustrated in FIG. 1, herein, and a memory system 504, which can be analogous to the memory system 104, 204, 304, 404 illustrated in FIGS. 1-4, herein. In some embodiments, the mobile computing device 501 can be analogous to the computing system 100 and/or the computing system 200 illustrated in FIGS. 1 and 2, respectively, herein. Embodiments are not so limited, however, and other areas of interest can include a nasal cavity, a stomach, a liver, a kidney, a lung, a brain, a muscle, a joint, a bone, and/or a ligament, among others.

The human medical self-diagnostic test subject 540 can include various areas of interest, such as the area of interest 541 with respect to performance of medical self-diagnostic testing operations, as indicated by the arrow between the mobile computing device 501 and the human medical self-diagnostic test subject 540. The area of interest 542 can be a blood vein 542 through which blood cells 544-1, 544-2 to 544-N and/or 546-1 to 546-M are flowing.

As shown in FIG. 5, the imaging device 521 can receive information (e.g., images and/or video) related to the area of interest 541. The information can be processed and/or analyzed within the mobile computing device 501 for example, using the memory system 504 resident on the mobile computing system 501. In some embodiments, the information (e.g., the images and/or video) can be processed by the mobile computing device 501 as part of performance of a medical self-diagnostic test.

The information, which can include images and/or streaming (e.g., live-streaming) video of the blood cells 544, 546 can be processed by the mobile computing system 501 in connection with execution of one or more applications to detect abnormalities in the blood cells 544, 546 that are running on the mobile computing device 501. In some embodiments, the blood cells 544 can indicate healthy blood cells, while the blood cells 546 can indicate blood cells in which an abnormality has been detected (e.g., blood cells that exhibit characteristics indicative of blood cancers such as leukemia, lymphoma myeloma, etc., fluctuating blood glucose levels, fluctuating blood pressure levels, percentages of white blood cells versus red blood cells, hemophilia, and/or anemia, among other abnormalities. As described above, execution of such applications can give rise to demanding workloads. Accordingly, as described herein, the information can be selectively written to different memory devices (e.g., the memory devices 223, 225, and/or 227 illustrated in FIG. 2, herein), and therefore different media types (e.g., the media types 224, 226, and/or 228 illustrated in FIG. 2, herein) based on characteristics of the workloads.

In some embodiments, the images and/or video can be processed and/or analyzed by the mobile computing device 501 during execution of an application to analyze the area of interest 541 illustrated in FIG. 5. Although shown as a single area of interest 541 for clarity, it will be appreciated that other portions of the human medical self-diagnostic test subject 540 can be analyzed. More specifically, any area of the human medical self-diagnostic test subject 540 that contains one or more blood veins 542 can be analyzed to detect abnormalities in the blood 544, 546 flowing through the blood vein(s) 542.

In addition, the images and/or video can be processed and/or analyzed by the mobile computing device 501 to detect and/or replace one or more corrupted portions (e.g., pixels) of the images and/or video to recover and/or improve the quality of the images and/or video as part of execution of the application to detect abnormalities in the blood 544, 546 in the blood vein(s) 542. For example, if portions of the images and/or video are blurry or suffer from pixel degradation, the application to detect the abnormalities in the blood 544, 546 can perform operations to recover and/or replace pixels with the assistance of machine learning to improve the clarity and/or quality of the images and/or video prior to performance of operations to detect abnormalities in the blood 544, 546.

Figure 6:
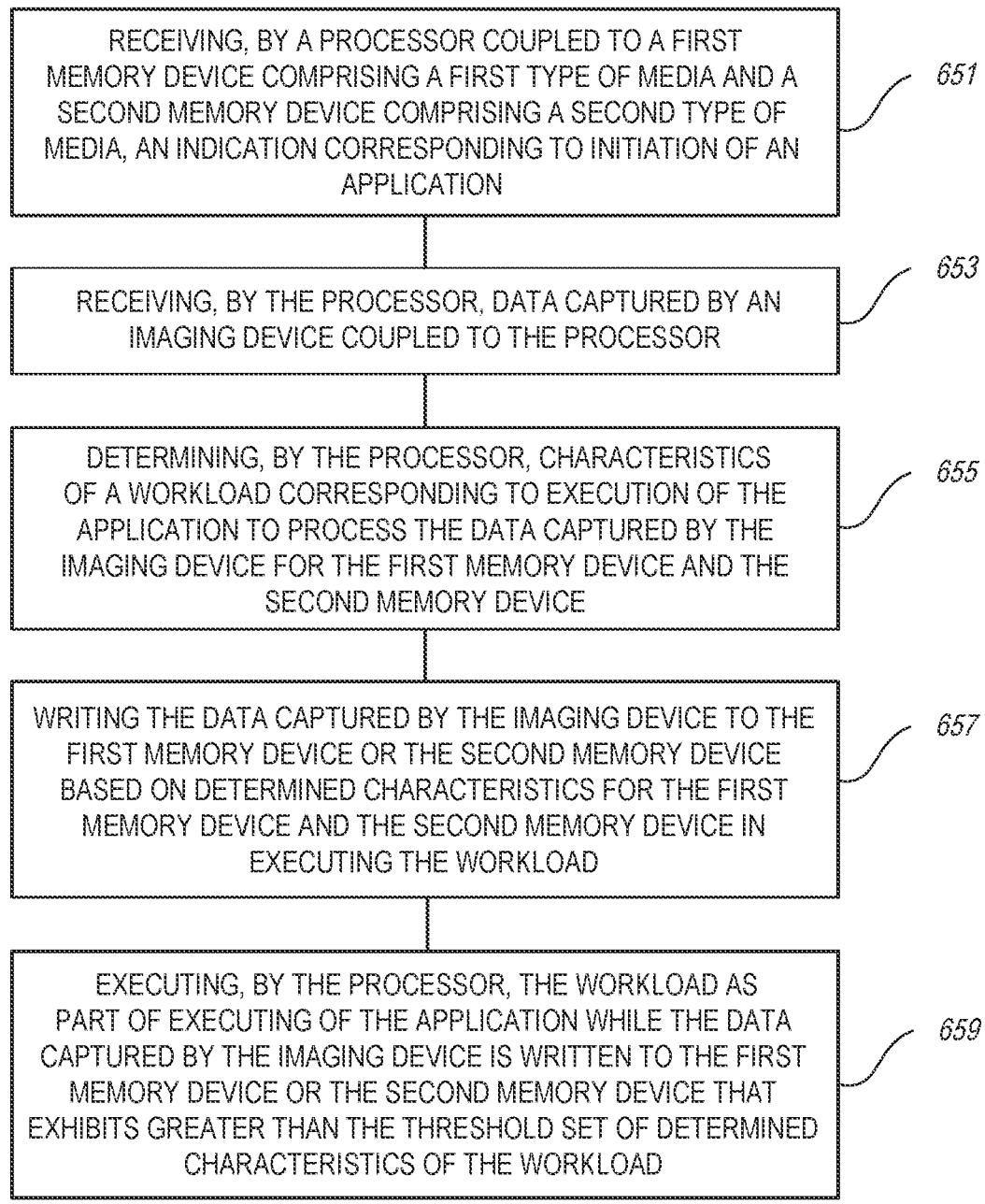
FIG. 6 is a flow diagram representing an example method corresponding to blood flow imaging in accordance with a number of embodiments of the present disclosure.

FIG. 6 is a flow diagram representing an example method corresponding to blood flow imaging in accordance with a number of embodiments of the present disclosure. The method 650 can be performed by processing logic that can include hardware (e.g., processor(s), processing device(s), control circuitry, dedicated logic, programmable logic, microcode, hardware of a device, and/or integrated circuit(s), etc.), software (e.g., instructions run or executed on a processor), or a combination thereof. Although shown in a particular sequence or order, unless otherwise specified, the order of the processes can be modified. Thus, the illustrated embodiments should be understood only as examples, and the illustrated processes can be performed in a different order, and some processes can be performed in parallel. Additionally, one or more processes can be omitted in various embodiments. Thus, not all processes are required in every embodiment. Other process flows are possible.

At block 651, the method 650 can include receiving, by a processor coupled to a first memory device comprising a first type of media and a second memory device comprising a second type of media, an indication corresponding to initiation of an application. In some embodiments, the indication corresponding to initiation of the application can be an application initiation indicator that indicates that execution of the application will involve processing of images that are larger than a threshold image size, higher in resolution than a threshold resolution, or higher in bandwidth consumption than a threshold image bandwidth consumption, or any combination thereof. The first memory device can be analogous to the memory device 123, 223, while the second memory device can be analogous to the memory device 125, 225 illustrated in FIGS. 1 and 2, herein. Further, the first type of media can be analogous to the media type 124, 224, while the second type of media can be analogous to the media type 126, 226 illustrated in FIGS. 1 and 2, herein.

In some embodiments, the method 650 can include reallocating computing resources amongst the first memory device and the second memory device responsive to receiving the indication corresponding to initiation of an application. For example, in embodiments in which the indication corresponding to initiation of the application is an application initiation indicator, computing resources can be reallocated between the first memory device and the second memory device to ensure that an adequate amount of computing resources that exhibit particular characteristics (e.g., the fastest memory access times among the memory devices, the highest bandwidth among the memory device, etc.) are available to store and process images that are to be captured by an imaging device.

At block 653, the method 650 can include receiving, by the processor, data captured by an imaging device coupled to the processor. In some embodiments, the data can include one or more images and/or video of blood flowing in a blood vein (e.g., the blood cells 544, 546 flowing in the blood vein 542 illustrated in FIG. 5, herein). That is, in some embodiments, the method 650 can include determining, by the processor, that the application corresponds to performance of an operation to detect an abnormality in at least a portion of a human body (e.g., the human medical self-diagnostic test subject 540 illustrated in FIG. 5, herein) and writing the data captured by the imaging device to the first memory device or the second memory device based, at least in part, on determining that the execution of the application corresponds to performance of the operation to detect the abnormality in at least the portion of the human body. The imaging device can be analogous to the imaging device 121, 521 illustrated in FIGS. 1 and 5, herein.

At block, 655, the method 650 can include determining, by the processor, characteristics of a workload corresponding to execution of the application to process the data captured by the imaging device for the first memory device and the second memory device. The characteristics of the workload can include an amount of computing resources consumed in execution of the workload, an amount of processing time involved in execution of the workload, or an amount of power consumed in execution of the workload, among others.

At block 657, the method 650 can include writing the data captured by the imaging device to the first memory device or the second memory device based on determined characteristics for the first memory device and the second memory device in executing the workload. In some embodiments, the characteristics of the first memory device and the second memory device can be determined prior to, or during, execution of the application. As described above, the determined characteristics of the first memory device and the second memory can include a bandwidth, a memory access time, a latency, a memory cell density, or any combination thereof, of the first memory device and the second memory device.

At block 659, the method 650 can include executing, by the processor, the workload as part of executing of the application while the data captured by the imaging device is written to the first memory device or the second memory device that exhibits greater than the threshold set of determined characteristics in executing the workload. In some embodiments, the operations (e.g., the operations 651, 653, 655, 657, and/or 659) of the method 650 can be performed in the absence of control signals generated external to the mobile computing device. Accordingly, in some embodiments, abnormalities in the blood can be detected and analyzed entirely within the mobile computing device without the need for transferring the data or processing responsibilities to circuitry external to the mobile computing device.

As described above, the method 650 can include transferring results corresponding to execution of the application to detect the abnormality in at least the portion of the human body to a hospital, a doctor's office, or an emergency service provider, or any combination thereof. This can allow for a doctor or other health care professional to maintain records of medical self-tests performed in accordance with embodiments of the present disclosure and/or can provide data to a medical professional for further analysis.

In some embodiments, the method 650 can include determining, by the processor, that the data captured by the imaging device corresponds to performance of an operation to detect an abnormality in at least a portion of a human body. The operation to detect the abnormality in the body can be performed as part of a self-diagnostic medical test. In such embodiments, the method 650 can further include writing at least the portion of the data associated with the workload and the data captured by the imaging device to the other of the first memory device or the second memory device based, at least in part, on determining that the workload or the data captured by the imaging device, or both, corresponds to performance of the operation to detect the abnormality in at least the portion of the human body.

In such embodiments, the method 650 can further include performing, by the processor, the operation to process the image or the video stream by exchanging at least one pixel of the image or the video stream, correcting a blurred portion of the image or the video stream, and/or removing noise from the image or the video stream.

As described above, the first memory device or the second memory device can be a non-persistent memory device, and the other of the first memory device or the second memory device can be a persistent memory device. In some embodiments, the processor, the first memory device, and the second memory device can be resident on a mobile computing device (e.g., the mobile computing device 501 illustrated in FIG. 5, herein). In such embodiments, the method 650 can include determining, writing, and causing, by the processor in the absence of control signals generated external to the mobile computing device. Embodiments are not so limited, and in some embodiments, the method 650 can include writing at least the portion of data associated with the workload to the other of the first memory device or the second memory device as part of an operation to optimize battery consumption of the mobile computing device.

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and processes are used. Therefore, the scope of one or more embodiments of the present disclosure should be determined with reference to the appended claims, along with the full range of equivalents to which such claims are entitled.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method, comprising:
receiving, by a processor coupled to a first memory device comprising a first type of media and a second memory device comprising a second type of media, an indication corresponding to initiation of an application;
receiving, by the processor, data captured by an imaging device coupled to the processor;
determining, by the processor, characteristics of a workload corresponding to execution of the application to process the data captured by the imaging device for the first memory device and the second memory device;
writing the data captured by the imaging device to the first memory device or the second memory device based on determined characteristics for the first memory device and the second memory device in executing the workload; and
executing, by the processor, the workload as part of executing of the application while the data captured by the imaging device is written to the first memory device or the second memory device that exhibits greater than the threshold set of determined characteristics in executing the workload.

2. The method of claim 1, further comprising reallocating computing resources amongst the first memory device and the second memory device responsive to receiving the indication corresponding to initiation of an application.

3. The method of claim 1, wherein the data captured by the imaging device includes one or more images of blood flowing in a blood vein, and wherein the data is captured by the imaging device when the imaging device is external to the blood vein.

4. The method of claim 1, further comprising:
determining, by the processor, that the application corresponds to performance of an operation to detect an abnormality in at least a portion of a human body; and
writing the data captured by the imaging device to the first memory device or the second memory device based, at least in part, on determining that the execution of the application corresponds to performance of the operation to detect the abnormality in at least the portion of the human body.

5. The method of claim 4, further comprising transferring results corresponding to execution of the application to detect the abnormality in at least the portion of the human body to a hospital, a doctor's office, or an emergency service provider, or any combination thereof.

6. The method of claim 1, wherein the processor, the first memory device, and the second memory device are resident on a mobile computing device, and wherein the method comprises receiving, determining, writing, and executing, by the processor, in the absence of control signals generated external to the mobile computing device.

7. The method of claim 1, further comprising determining characteristics of the first memory device and the second memory device prior to, or during, execution of the application, wherein the determined characteristics of the first memory device and the second memory include a bandwidth, a memory access time, a latency, a memory cell density, or any combination thereof, of the first memory device and the second memory device.

8. The method of claim 1, wherein the indictor corresponding to initiation of the application comprises an indication that execution of the application will involve processing of images that are larger than a threshold image size, higher in resolution than a threshold resolution, or higher in bandwidth consumption than a threshold image bandwidth consumption, or any combination thereof.

9. An apparatus, comprising:
a first memory device comprising a first type of media;
a second memory device comprising a second type of media;
an imaging device; and
a processor coupled to the first memory device, the second memory device, and the imaging device, wherein the processor is to:
receive an application initiation indicator;
reallocate computing resources among the first memory device and the second memory device based, at least in part, on determined characteristics of the first memory device and the second memory device in response to receipt of the application initiation indicator;
receive data captured by an imaging device;
write the data captured by the imaging device to the first memory device or the second memory device based on the determined characteristics for the first memory device and the second memory device;
execute the application while the data captured by the imaging device is written to the first memory device or the second memory device.

10. The apparatus of claim 9, wherein the application initiation indicator comprises signaling indicative of performance of operations to processing of images that are larger than a threshold image size, higher in resolution than a threshold resolution, or higher in bandwidth consumption than a threshold image bandwidth consumption, or any combination thereof.

11. The apparatus of claim 9, wherein the processor is to:
receive a sequence of images as part of receipt of the data captured by the imaging device; and
process the sequence of images to exchange at least one pixel of at least one image of the sequence of images, correct a blurred portion of the at least one image of the sequence of images, or remove noise from the at least one image of the sequence of images, or any combination thereof.

12. The apparatus of claim 9, wherein:
the processor is to determine the characteristics of the first memory device and the second memory device prior to, or during, execution of the application, and
the determined characteristics of the first memory device and the second memory device include a bandwidth, a memory access time, a latency, a memory cell density, or any combination thereof, of the first memory device and the second memory device.

13. The apparatus of claim 9, wherein the processor, the imaging device, the first memory device, and the second memory device are resident on a mobile computing device, and wherein the processor is to:
receive images of blood flow in a blood vein as part of the data captured by the imaging device; and
execute the application to determine whether an abnormality is detected in the received images of the blood flow.

14. The apparatus of claim 9, wherein the processor, the imaging device, the first memory device, and the second memory device are resident on a mobile computing device, and wherein the processor is to execute one or more sets of machine learning instructions to: determine that the application initiation indicator corresponds to execution of an application to process data captured by the imaging device that exceeds a threshold quantity of pixels, or
determine the characteristics of the first memory device and the second memory device, or both.

15. The apparatus of claim 9, wherein the first type of media and the second type of media comprise sets of memory cells that exhibit different storage characteristics.

16. The apparatus of claim 9, wherein the first memory device or the second memory device is a non-persistent memory device, and wherein the other of the first memory device or the second memory device is a persistent memory device.

17. The apparatus of claim 9, wherein:
the processor, the imaging device, the first memory device, and the second memory device are resident on a mobile computing device,
the first memory device or the second memory device is a NAND flash memory device that comprises a set of single level memory cells (SLCs) and a set of multi-level memory cells (MLCs),
the set of SLCs are configured to store a look-up table to facilitate writing of at least the portion of the data to the other of the first memory device or the second memory device, and
the processor is to write at least a portion of the data captured by the imaging device to the set of SLC memory cells or the set of MLC memory cells based, at least in part, on receipt of the application initiation indicator.

18. A system, comprising:
a memory system comprising a processor, a first memory device comprising a first type of media, a second memory device comprising a second type of media, and a third memory device comprising a third type of media; and
an imaging device coupled to the memory device, wherein the processor is to:
receive one or more images captured by the imaging device;
generate, based on characteristics of the one or more received images, an application initiation indicator corresponding to execution of an application corresponding to detection of an abnormality in at least a portion of a living creature;
reallocate computing resources among the first memory device, the second memory device, or the third memory device, or any combination thereof based, at least in part, on characteristics of the first memory device, the second memory device, and the third memory device in response to generation of the application initiation indicator;

write at least a portion of the one or more images captured by the imaging device to the first memory device, the second memory device, or the third memory device, or combinations thereof in response to generation of the application initiation indicator; and execute the application corresponding to detection of the abnormality in at least the portion of the living creature while the one or more images captured by the imaging device are written to the first memory device, the second memory device, or the third memory device, or any combination thereof.

19. The system of claim 18, wherein:

the first media type comprises an array of memory cells that include at least one capacitor and at least one transistor, the second media type comprises an array of floating-gate metal-oxide-semiconductor field-effect transistors, and the third type of media comprises an array of resistance variable memory cells that are configured to perform bit storage based on a change in a bulk resistance associated with the resistance variable memory cells.

20. The system of claim 18, wherein the memory system and the imaging device are resident on a mobile computing device, and wherein the processor is to transfer results corresponding to execution of the application to detect the abnormality in at least the portion of the living creature to a hospital, a doctor's office, or an emergency service provider, or any combination thereof.

21. The system of claim 18, wherein the memory system and the imaging device are resident on a mobile computing device that further comprises a display screen, and wherein the processor is to:

generate dietary recommendations based, at least in part, on results of execution of the application to detect the abnormality in at least the portion of the living creature; and display the dietary recommendations on the display screen.

22. The system of claim 18, wherein:

the processor is to determine the characteristics of the first memory device, the second memory device, and the third memory device prior to, or during, execution of the application, and the determined characteristics of the first memory device, the second memory device, and the third memory device include a bandwidth, a memory access time, a latency, a memory cell density, or any combination thereof, of the first memory device, the second memory device, and the third memory device.

23. The system of claim 18, wherein:

the processor, the imaging device, the first memory device, and the second memory device are resident on a mobile computing device, and the processor is to execute one or more sets of machine learning instructions to: determine the characteristics of the first memory device, the second memory device, and the third memory device based, at least in part, on monitored benchmark data associated with the first memory device, the second memory device, and the third memory device; and reallocate the computing resources among the first memory device, the second memory device, or the third memory device, or any combination thereof based, at least in part, on the determined characteristics of the first memory device, the second memory device, and the third memory device.

24. The system of claim 18, wherein:

the processor, the imaging device, the first memory device, and the second memory device are resident on a mobile computing device, and the processor is to execute one or more sets of machine learning instructions to:

determine characteristics of the one or more received images based on images previously captured by the imaging device; and generate the application initiation indicator based on the determined characteristics of the one or more images.

25. The system of claim 18, wherein at least a portion of data corresponding to the one or more images captured by the imaging device is written to the first memory device, the second memory device, or the third memory device according to a universal number format or a posit format.

* * * * *